US00PP12076P2

(12) United States Plant Patent
Yates

(10) Patent No.: US PP12,076 P2
(45) Date of Patent: Sep. 4, 2001

(54) ERIGERON PLANT NAMED 'SEA BREEZE'

(76) Inventor: Frederick Yates, A. T. Yates & Son, Poplars Nursery, Holmes Chapel Rd., Somerford, Congleton, Cheshire CW12 4SP (GB)

( * ) Notice: Subject to any disclaimer, the term of this patent is extended or adjusted under 35 U.S.C. 154(b) by 0 days.

(21) Appl. No.: 09/321,648

(22) Filed: May 28, 1999

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Anne Marie Grünberg
(74) *Attorney, Agent, or Firm*—Mark P. Bourgeois

(57) ABSTRACT

A new cultivar of *Erigeron glaucus* named 'Sea Breeze' that is characterized in having large and consistent rich red-purple flowers and a compact growth habit.

1 Drawing Sheet

BACKGROUND OF THE INVENTION

The present invention relates to a new and distinct cultivar of *Erigeron glaucus* and will be referred to hereafter as 'Sea Breeze' represents a new variety of Seaside Daisy, a perennial herb grown for landscape use.

The new Erigeron was selected by the inventor from a seed bed of unidentified and unpatented hybrids of *Erigeron glaucus* in a cultivated area of Congleton, Cheshire, England in 1992. The primary criteria for selecting 'Sea Breeze' was good strong flower color and a compact habit of growth as compared to the species and other known cultivars. The closest comparative cultivar is 'Four Winds' (not patented). 'Four Winds' has smaller leaves and smaller flowers as compared to 'Sea Breeze'.

Asexual reproduction of the new cultivar was first accomplished by taking cuttings in Congleton, Chesire, England on July 1993 by the inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish this cultivar from other commercial varieties.

1. The flower color of 'Sea Breeze' is a rich, red-purple color. *Erigeron glaucus* flowers are typically lavender to a lavender-pink color. The color of 'Four Winds' is typical of the species.

2. 'Sea Breeze' has a compact growth habit. *Erigeron glaucus* has lanky flower stems and longer, strap-like leaves.

3. The flowers of 'Sea Breeze' are larger than typical. 'Sea Breeze' flowers are 4.2 to 4.5 cm in diameter whereas the flowers of 'Four Winds' are 2.0 to 2.5 cm in diameter.

BRIEF DESCRIPTION OF THE DRAWING

The drawing illustrates the overall appearance of the new Erigeron plant 'Sea Breeze', showing the colors as true as it is reasonably possible to obtain in colored reproductions of this type. The drawing shows a side perspective view of 'Sea Breeze'in a two gallon container. The photograph may appear different from the actual colors due to light reflectance.

BOTANICAL DESCRIPTION OF THE PLANT

The botanical description and measurements describe a 6 month old plant in a one gallon container grown in a greenhouse in Encinitas, Calif., under natural lighting with an average temperature of 70 degrees F. with a constant feed of 12-12-12fertilizer at a rate of 300 ppm Nitrogen. Phenotypic differences may be observed with variations in environmental, climatic, and cultural conditions. The color determination is in accordance with the R.H.S. Colour Chart of The Royal Horticultural Society, London, England, except where general color terms of ordinary dictionary significance are used.

Botanical classification: 'Sea Breeze' is a cultivar of *Erigeron glaucus*. Compositae family.
Commercial classification: Seaside Daisy.
Parentage:
- *Female parent.*—Unidentified *Erigeron glaucus* (not patented).
- *Male parent.*—Unidentified *Erigeron glaucus* (not patented).

Plant description:
- *Blooming period.*—May to September in the UK.
- *Plant habit.*—Rounded mound, clump-forming.
- *Height and spread.*—20–25 cm in height, spread is up to 30 cm.
- *Hardiness.*—Zone 5 (possibley 4).
- *Type.*—Tufted perennial herb.
- *Root system.*—Fibrous.
- *Time to initiate new roots.*—6–10 days at 68° C. under mist.
- *Time to develop roots.*—6–8 weeks in a 2" cell, with 2 weeks under mist.
- *Vigor.*—Moderately vigorous.
- *Propagation.*—Cuttings.
- *Culture.*—Sunny location in well-drained, moderately fertile soils.
- *Diseases and Pests.*—No known unique susceptibilty or resistance.

Stems: Shape: Round, somewhat succulent.
- *Size.*—Main stem 1 cm in diameter, secondary stems to 0.5 cm in diameter and tend to be in whorls.
- *Surface.*—Glandular-hairs.
- *Color.*—145A.

Leaves:

*Shape.*—Broadly spatulate, tapers to a winged petiole.

*Division.*—Simple.

*Base.*—Cuneate.

*Apex.*—Obtuse.

*Venation.*—Not prominent.

*Margins.*—Entire to sparsely dentate (1–4/leaves).

*Attachment.*—Decurrent.

*Arrangement.*—Scattered.

*Attitude.*—Upright to curved downward, broad end is concave with the tip curved downward.

*Surface.*—Glaucous.

*Size.*—Basal tufted foliage; 5.4–6.0 cm in length, 0.5 cm in width at the base and 1.5–2.5 cm at the widest point. flowering stems; up to 3.8 cm.

*Color.*—Upper and lower surface of immature foliage 144A, upper surface of mature foliage 189A, lower surface of mature foliage 191A.

Flowers:

*Type.*—Composite capitulum, solitary to cymose (2–3 typically).

*Lastingness of flowers.*—2–3 weeks.

*Persistence.*—Not self-cleaning, receptacle and phyllaries are persistent.

*Size.*—4.2–4.8 cm: Disk; 1.8–2.0 cm. Ray (semi-double); 1.5 cm in length. 1–0.2 cm in width. Calyx: composed of a pappus of bristles, separate, very fine: 1 mm in diameter, 3.0 mm in length, 15–20 in number, translucent white. Color: Disk matures from 144A to 14B, (stamens 7A, brown at maturity 166D). Ray opens 57D, matures to 66D.

Flower bud: Oval with flattened apex, 189B, hairy, 0.7 cm in length, 0.8 cm in width.

Phyllaries:

*Type.*—Imbricate bracts in two layers, approximately 32 in number, color, 191A, 1.0 cm in length, 1.0 mm in width.

*Receptacle.*—Flat 144A in color, 0.5 cm in Diameter.

Reproduction organs:

*Androecium.*—Present on disc florets only, 5 stamens, basifixed, filament color 2C, filament length 3.0 mm, anther color 7A, pollen color 7 A maturing to 165B, amount of pollen: Moderate.

*Gynoecium.*—Present on ray and disc florets.

*Pistil number.*—One, stigmas bifid, Pistil length: about 4 mm.

*Style length.*—about 3 mm, Pistil color 145C,

*Ovary.*—Superior 165C.

Fruit:

*Type.*—Compressed Achene, with 6 very fine pappus per Achene.

*Number.*—Approximately 100 per flower.

*Color.*—164D.

*Achene size.*—3 mm in width at apex, 0.25 mm in width at the base, 1.0 mm in length.

Seed: One seed per Achene. Endosperm absent, embryo 1.0 mm in length, 0.25 mm in width, embryo color 164B.

I claim:

1. A new and distinct cultivar of *Erigeron glaucus* plant named 'Sea Breeze' as described and illustrated.

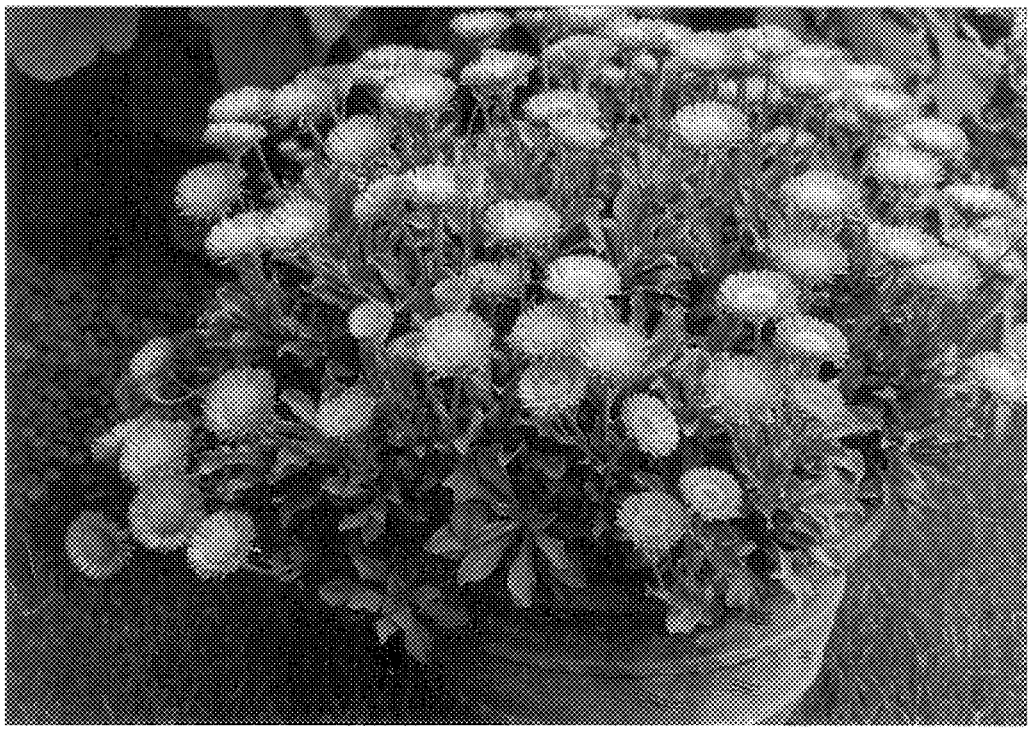
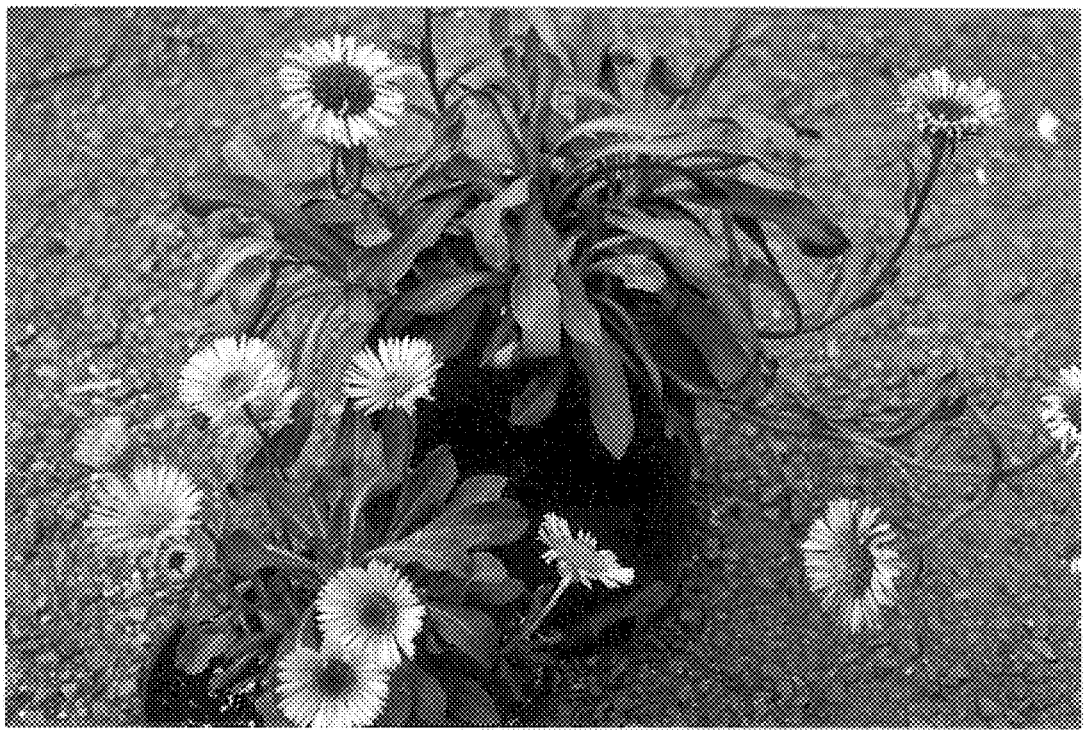

* * * * *